(12) United States Patent
Lee (10) Patent No.: US 12,171,895 B2
(45) Date of Patent: Dec. 24, 2024

(54) PORTABLE STERILIZATION AND DISINFECTION APPARATUS FOR STERILIZING AND DISINFECTING SPACE

(71) Applicant: LGS CORPORATION Co., Ltd., Gwangmyeong-si (KR)

(72) Inventor: Chul Kyu Lee, Gunpo-si (KR)

(73) Assignee: LGS CORPORATION Co., Ltd., Gwangmyeong-si (KR)

(*) Notice: Subject to any disclaimer, the term of this patent is extended or adjusted under 35 U.S.C. 154(b) by 781 days.

(21) Appl. No.: 17/383,473

(22) Filed: Jul. 23, 2021

(65) Prior Publication Data

US 2022/0096689 A1  Mar. 31, 2022

(30) Foreign Application Priority Data

Sep. 29, 2020 (KR) .................. 10-2020-0127318
Mar. 12, 2021 (KR) .................. 10-2021-0032366

(51) Int. Cl.
*A61L 2/22* (2006.01)
*A61L 2/26* (2006.01)
*H01M 50/244* (2021.01)

(52) U.S. Cl.
CPC .................. *A61L 2/22* (2013.01); *A61L 2/26* (2013.01); *H01M 50/244* (2021.01); *A61L 2202/14* (2013.01); *A61L 2202/15* (2013.01); *A61L 2202/16* (2013.01); *A61L 2202/25* (2013.01); *H01M 2220/30* (2013.01)

(58) Field of Classification Search
CPC ..... A61L 2/18; A61L 2/20; A61L 2/22; A61L 2/24; A61L 2/26; A61L 9/03; A61L 9/032; A61L 9/14; A61L 2202/14; A61L 2202/15; A61L 2202/16; A61L 2202/25
See application file for complete search history.

(56) References Cited

U.S. PATENT DOCUMENTS

| | | | |
|---|---|---|---|
| 6,550,651 B1* | 4/2003 | Murdoch ............. | A45C 13/262 224/580 |
| 2013/0078143 A1* | 3/2013 | Hill ..................... | A61L 2/186 422/292 |
| 2015/0117955 A1* | 4/2015 | Houston ............... | B09C 1/08 405/129.9 |
| 2020/0054000 A1* | 2/2020 | Zwahlen ............... | B05B 13/005 |
| 2021/0331187 A1* | 10/2021 | Youngblut ............ | B05B 15/652 |

FOREIGN PATENT DOCUMENTS

KR    101230753 B1 *  2/2013

OTHER PUBLICATIONS

English-language machine translation of KR-101230753-B1 (Year: 2013).*

* cited by examiner

*Primary Examiner* — Timothy C Cleveland
(74) *Attorney, Agent, or Firm* — Revolution IP, PLLC (57) ABSTRACT

Disclosed is a portable sterilization and disinfection apparatus for sterilizing and disinfecting a space, wherein the portable sterilization and disinfection apparatus may enable ultrafine spray and accurate oriented spray, may expand a spraying distance, and may be freely moved to any space so as to effectively sterilize and disinfect the space.

4 Claims, 9 Drawing Sheets

PORTABLE STERILIZATION AND DISINFECTION APPARATUS FOR STERILIZING AND DISINFECTING SPACE

BACKGROUND OF THE INVENTION

Field of the Invention

The present invention relates to a portable spray-type sterilization and disinfection apparatus which may sterilize and disinfect a space, and more particularly, to a portable sterilization and disinfection apparatus for sterilizing and disinfecting a space, which may enable ultrafine spray and accurate oriented spray, may expand a spraying distance, and may be freely moved to any space so as to effectively sterilize and disinfect the space.

Description of the Related Art

Sterilization refers to any process that removes, kill or destructs of bacteria, germs, viruses or microorganisms and, in general, sterilization methods are roughly classified into physical methods including a heating method that sterilizes a target to be sterilized through heating using heat or steam, and chemical methods that sterilize a target to be sterilized using sterilizers, sterilizing gases, etc. Recently, as recognition of bacteria and interest in health are gradually increasing among ordinary persons, interest in apparatuses and/or methods for easily performing sterilization is also increasing.

In the physical methods generally used to remove bacteria, germs, viruses or microorganisms, heat or steam having a high temperature is applied to a target to be sterilized so as to remove bacteria, germs, viruses or microorganisms, but time and fuel taken to secure the high temperature are required and thus it takes a long time to sterilize the target. Further, a user may frequently get burned by heat or steam of the high temperature, and thus, it is difficult to use the physical methods.

On the other hand, as the chemical methods which sterilize a target to be sterilized using sterilizers, sterilizing gases, etc., a sterilizer or a sterilizing gas formed of a chemical substance having the sterilizing effect is generally used.

As sterilization using the chemical methods, there is a method in which, when a target area is small, a worker carries a spray including a storage tank and a pump device, integrally connected to each other, over his/her shoulder, and sprays a sterilizer by pumping. However, this method causes cumbersomeness and sprays only a small amount of the sterilizer, and thus recently has a limit in sterilization and disinfection of a wide space.

In order to sterilize and disinfect a wide space, a method in which a spray-type sterilization and disinfection apparatus is used in the state of being mounted in a vehicle or a handcart is used. However, this method has a limit to moving freely, and sterilization and disinfection are performed in only one direction through a spray pipe which is generally installed in a straight linear direction.

Therefore, research and development of a sterilization and disinfection apparatus, which may perform spray of a large amount so as to sterilize and disinfect a wide space, may have free orientation in terms of a spraying direction, and may secure a sprayed droplet size for effective sterilization, are required.

SUMMARY OF THE INVENTION

Therefore, the present invention has been made in view of the above problems, and it is an object of the present invention to provide a portable sterilization and disinfection apparatus for sterilizing and disinfecting a space, which may enable sterilization and disinfection of a wide space as well as simple insecticide action and disinfection, may enable ultrafine spray so as to prevent droplets caused by spray from falling around the apparatus, may enable freely oriented spray in all direction, may expand a spraying direction, and may be freely moved to any region or space.

It is another object of the present invention to provide a portable sterilization and disinfection apparatus for sterilizing and disinfecting a space, which may automatically control sterilization and disinfection according to surrounding environments, such as temperature and humidity, so as to effectively sterilize and disinfect the space.

In accordance with the present invention, the above and other objects can be accomplished by the provision of a portable sterilization and disinfection apparatus for sterilizing and disinfecting a space, the portable sterilization and disinfection apparatus including a chemical liquid supply device configured to store a chemical liquid for sterilization and disinfection and to supply the stored chemical liquid for sterilization and disinfection to a sterilization and disinfection device, and the sterilization and disinfection device connected to the chemical liquid supply device through a chemical liquid supply line and configured to receive the chemical liquid for sterilization and disinfection from the chemical liquid supply device, to atomize the chemical liquid for sterilization and disinfection, and to discharge the chemical liquid for sterilization and disinfection.

The chemical liquid supply device may include a box-shaped body, a body cover combined with the body so as to open and close the body, a chemical liquid storage tank provided within the body, a pump provided within the body and configured to pump the chemical liquid for sterilization and disinfection from the chemical liquid storage tank so as to supply the chemical liquid for sterilization and disinfection to the sterilization and disinfection device, a battery unit provided within the body and configured to provide power required to operate the pump, and a control switch provided on the body and configured to control operation of the pump.

The body may include a handle member provided at one side of an upper end of the body or an upper end of a rear surface of the body and configured to extend and contract in a telescopic manner so as to be received in the body, and rolling wheels provided at a lower end of the body, and the body cover may be configured to open and close the body in a sliding manner.

The battery unit may include a battery support provided at one side of a lower portion of the body, and a battery detachably fixed to the battery support, and the battery support may be provided on an inner wall of one side of the lower portion of the body so as to be foldable at an angle of 90°.

The sterilization and disinfection device may include a casing provided with a first grill member and a second grill member provided at both ends of the casing so that air is flowable outwards therethrough, a handle frame formed at one side of the casing and configured to be grasped by a worker, and an atomization blower unit provided at one end of the casing and configured to atomize the chemical liquid for sterilization and disinfection supplied from the chemical liquid supply device and to discharge the atomized chemical liquid for sterilization and disinfection.

The atomization blower unit may include a distribution pipe provided within one end of the casing and configured to have a connector connected to the chemical liquid supply line, a plurality of nozzles provided at the distribution pipe and configured to atomize the chemical liquid for sterilization and disinfection and to discharge the atomized chemical liquid for sterilization and disinfection, a blower fan provided within a remaining end of the casing and operated to blow air, a control circuit module provided on the handle frame and configured to control operation of the blower fan, a fan speed control switch provided on the handle frame and configured to control turning-on/off of the blower fan and a speed of the blower fan, and a fan battery provided within the casing and configured to provide power required to operate the blower fan.

The atomization blower unit may include a distribution pipe provided within one end of the casing and configured to receive the chemical liquid for sterilization and disinfection, a chemical liquid connection port provided in the handle frame and configured such that the chemical liquid supply line is connected to the chemical liquid connection port, a supply pipe provided between the distribution pipe and the chemical liquid connection port so as to connect the distribution pipe and the chemical liquid connection port, a plurality of nozzles provided at the distribution pipe and configured to atomize the chemical liquid for sterilization and disinfection and to discharge the atomized chemical liquid for sterilization and disinfection, a blower fan provided within the casing and operated to blow air, a control circuit module provided on the handle frame and configured to control operation of the blower fan, a fan speed control switch configured to control turning-on/off of the blower fan and a speed of the blower fan, and a fan battery provided within the casing and configured to provide power required to operate the blower fan.

The distribution pipe may be formed as a ring-shaped pipe and be fixed such that an outer circumferential surface thereof is spaced apart from an inner wall of the casing, and the portable sterilization and disinfection apparatus may further include temperature and humidity sensors provided on the casing and configured to transmit detected signals to the control circuit module, and a heating member configured to perform heating by a control signal from the control circuit module.

The casing may include a linear pipe-shaped part configured to form a central portion of the casing, a first expansion pipe part having a conical shape and provided at one end of the linear pipe-shaped part, a second expansion pipe part having a conical shape and provided at a remaining end of the linear pipe-shaped part, and a power connection port configured such that a power cable is connected thereto so as to supply power to the control circuit module may be formed in the handle frame.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Additional objects, features and advantages of the present invention will become apparent from the descriptions of aspects hereinbelow with reference to the accompanying drawings.

Hereinafter, a portable sterilization and disinfection apparatus for sterilizing and disinfecting a space according to an exemplary embodiment of the present invention will be described in detail with reference to the accompanying drawings.

Figure 1:
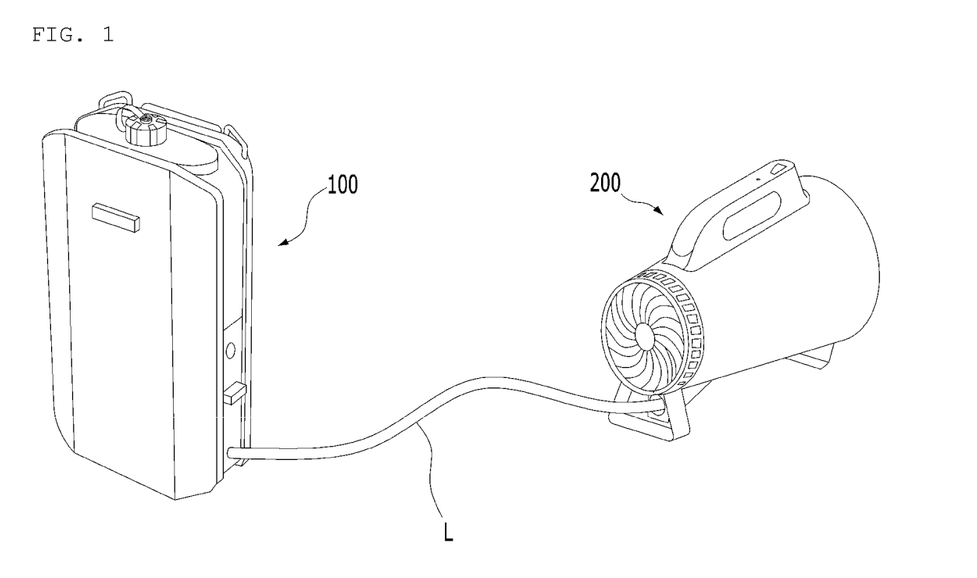
FIG. 1 is a perspective view illustrating the overall configuration of a portable sterilization and disinfection apparatus for sterilizing and disinfecting a space according to the present invention.

FIG. 1 is a perspective view illustrating the overall configuration of a portable sterilization and disinfection apparatus for sterilizing and disinfecting a space according to the present invention.

The portable sterilization and disinfection apparatus according to the present invention roughly includes, as shown in FIG. 1, a chemical liquid supply device 100 and a sterilization and disinfection device 200.

Concretely, the portable sterilization and disinfection apparatus according to the present invention includes, as shown in FIG. 1, the chemical liquid supply device 100 configured to supply a chemical liquid for sterilization and disinfection stored therein to the sterilization and disinfection device 200, and the sterilization and disinfection device 200 connected to the chemical liquid supply device 100 through a chemical liquid supply line L and configured to receive the chemical liquid for sterilization and disinfection from the chemical liquid supply device 100, to atomize the chemical liquid for sterilization and disinfection and to discharge the atomized chemical liquid for sterilization and disinfection.

The chemical liquid supply device 100 will be described in detail with reference to FIGS. 2 to 7.

Figure 2:
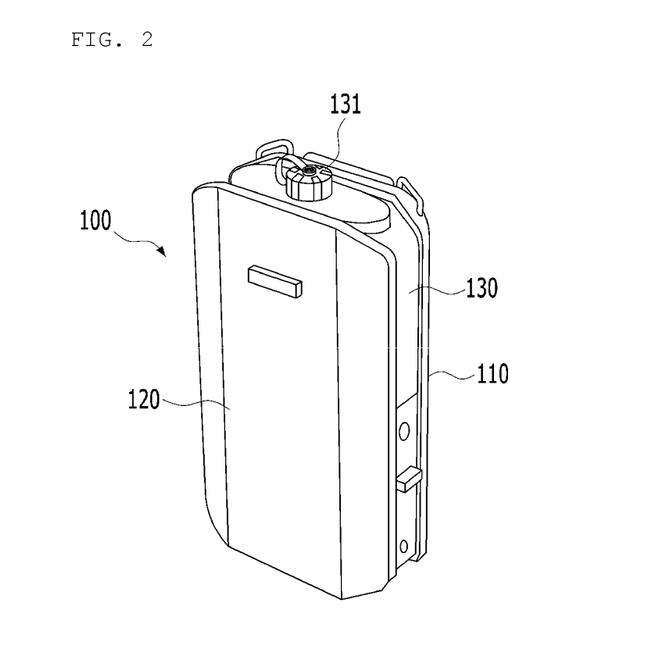
FIG. 2 is a perspective view of a chemical liquid supply device included in a portable sterilization and disinfection apparatus according to one embodiment of the present invention, as seen from one side.
Figure 3:
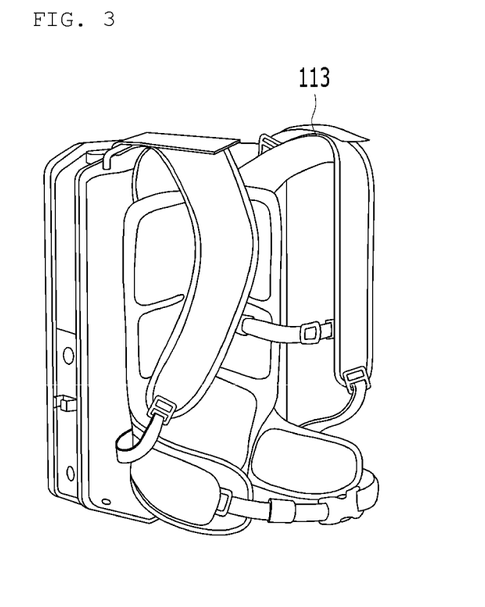
FIG. 3 is a perspective view of the chemical liquid supply device included in the portable sterilization and disinfection apparatus according to one embodiment of the present invention, as seen from the other side.
Figure 4:
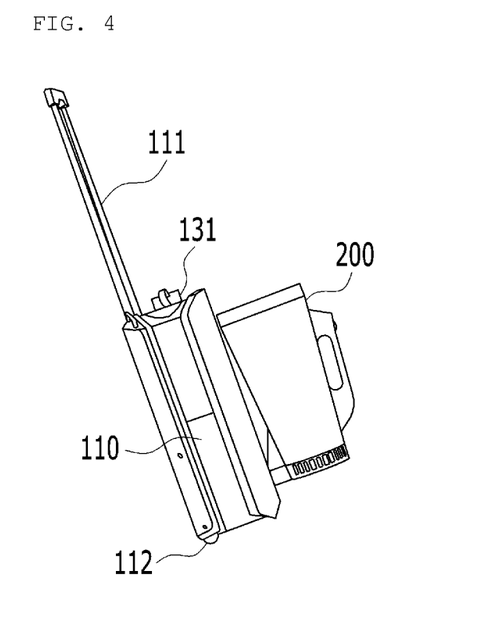
FIG. 4 is a side view of a chemical liquid supply device included in the portable sterilization and disinfection apparatus according to another embodiment of the present invention.
Figure 5:
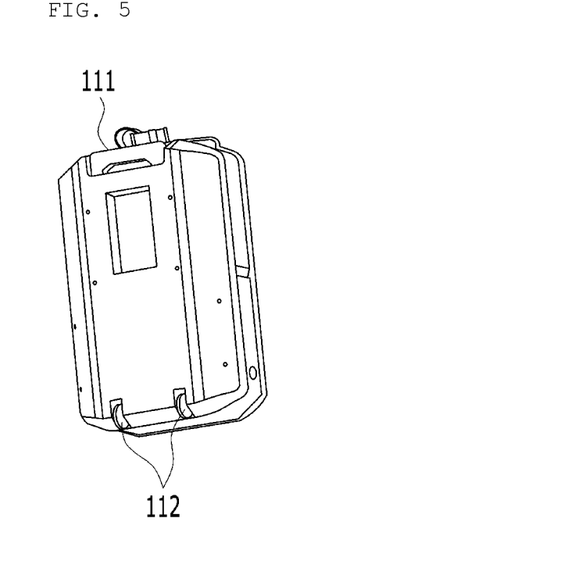
FIG. 5 is a perspective view of the chemical liquid supply device included in the portable sterilization and disinfection apparatus according to another embodiment of the present invention, as seen from one side.
Figure 6:
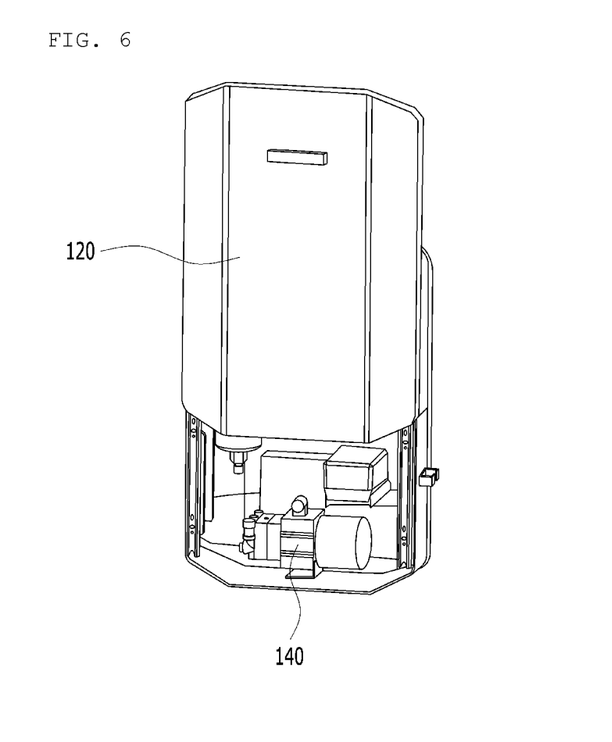
FIG. 6 is a perspective view illustrating an opening and closing structure of the chemical liquid supply device included in the portable sterilization and disinfection apparatus according to the present invention.
Figure 7:
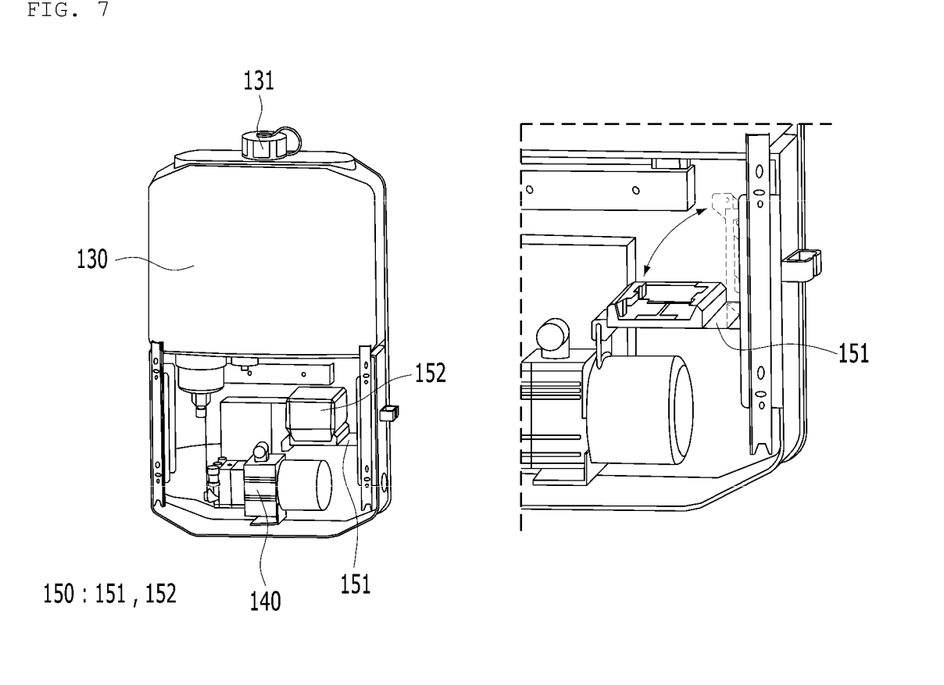
FIG. 7 is a view illustrating the inner configuration of the chemical liquid supply device included in the portable sterilization and disinfection apparatus according to the present invention.

FIG. 2 is a perspective view of a chemical liquid supply device included in a portable sterilization and disinfection apparatus according to one embodiment of the present invention, as seen from one side, FIG. 3 is a perspective view of the chemical liquid supply device included in the portable sterilization and disinfection apparatus according to one embodiment of the present invention, as seen from the other side, FIG. 4 is a side view of a chemical liquid supply device included in the portable sterilization and disinfection apparatus according to another embodiment of the present invention, FIG. 5 is a perspective view of the chemical liquid supply device included in the portable sterilization and disinfection apparatus according to another embodiment of the present invention, as seen from one side, FIG. 6 is a perspective view illustrating an opening and closing structure of the chemical liquid supply device included in the portable sterilization and disinfection apparatus according to the present invention, and FIG. 7 is a view illustrating the inner configuration of the chemical liquid supply device included in the portable sterilization and disinfection apparatus according to the present invention.

The chemical liquid supply device 100 includes a box-shaped body 100 having one open surface, a body cover 120 combined with the body 110 so as to open and close an opening formed by the open surface of the body 100, a chemical liquid storage tank 130 provided within the body 110, a pump 140 provided within the body 110 and configured to receive the chemical liquid for sterilization and disinfection from the chemical liquid storage tank 130 through an inlet 141 and to pump the chemical liquid for sterilization and disinfection through an outlet 142 connected to the chemical liquid supply line L, a battery unit 150 provided at one side of the inside of the body 110 so as to provide power required to operate the pump 140, and a control switch (not shown) provided at one side of the body 110 so as to turn the pump 140 on and off.

The body 110 may be formed in, for example, the form of a rectangular box, one wall surface of which is open, but is not limited thereto.

The body 110 may be provided with a pair of shoulder straps 113 so that a worker is capable of carrying the chemical liquid supply device 100 over his/her shoulder.

Further, the body 110 includes a handle member 111, which is provided at one side of the upper end of the body 110 or the upper end of the rear surface of the body 110 and extends and contracts in a telescopic manner so as to be received in the body 110, as shown in FIGS. 4 and 5. Further, rolling wheels 112 may be provided at the lower end of the body 110 so that the chemical liquid supply device 100 is movable on the ground.

The body cover 120 opens and closes the opening of the body 110, and may employ any element configured to fix the body cover 120 in the closed state thereof without being limited thereto.

For example, the body cover 120 may be provided to open and close the opening of the body 110 in a sliding manner, as shown in the drawings. Further, the body cover 120 may be configured such that one side of the body cover 120 is combined with one side of the body 110 by a hinge part and the other side of the body cover 120 is rotated about the axis of the hinge part so as to open and close the opening of the body 110, and the closed state of the body cover 120 is fixed using a clamping part.

The chemical liquid storage tank 130 may be provided in the upper region of the inside of the body 110. The reason for this is to supply the chemical liquid for sterilization and disinfection stored in the chemical liquid tank 130 to the inlet 141 of the pump 140 using gravity.

Further, the chemical liquid storage tank 130 includes an injection hole formed at the upper part thereof so as to inject the chemical liquid for sterilization and disinfection into the chemical liquid storage tank 130, and a lid 131 configured to open and close the injection hole. Here, the body 110 is formed such that the lid 131 is exposed to the outside from the upper surface of the body 110.

The pump 140 is provided within the body 110, receives the chemical liquid for sterilization and disinfection from the chemical liquid storage tank 130 through the inlet 141, and pumps the chemical liquid for sterilization and disinfection through the outlet 142 so as to supply the chemical liquid for sterilization and disinfection to the sterilization and disinfection device 200 via the chemical liquid supply line L. In the present invention, the pump 140 may be a high pressure pump (for example, a plunger pump) having an operating pressure of 50 bar to 100 bar.

Further, the pump 140 may be mounted at the lower end of the body 110 so as to be located at the center of gravity of the chemical liquid supply device 100.

The battery unit 150, which is provided at one side of the inside of the body 110 and is configured to provide power required to operate the pump 140, includes a battery support 151 provided at one side of the lower portion of the body 110, and a battery 152 detachably fixed to the battery support 151.

The battery support 151 is provided on the inner wall of one side of the lower portion of the body 110, and is configured to be foldable at an angle of 90°. The reason for this is that the battery support 151 may be folded up after detaching the battery 152 from the battery support 151 so as to secure a space during maintenance and repair work.

In order to detachably fix the battery 152 to the battery support 151, well-known detachable fixing structures (for example, a detachable fixing structure using interference fit, a detachable fixing structure using clamping, etc.) may be employed, and a detailed description thereof will be omitted.

The control switch, which is provided at one side of the body 110 so as to turn the pump 140 on and off, may be provided at one side of one surface of the body 110, and may be configured to extend through a cable line. When the control switch is configured to extend through the cable line, a worker may easily operate the chemical liquid supply device 100 even in the state in which the worker carries the chemical liquid supply device 100 on his/her shoulder.

Thereafter, the sterilization and disinfection device 200 according to one embodiment of the present invention will be described in detail with reference to FIGS. 8 to 12.

Figure 8:
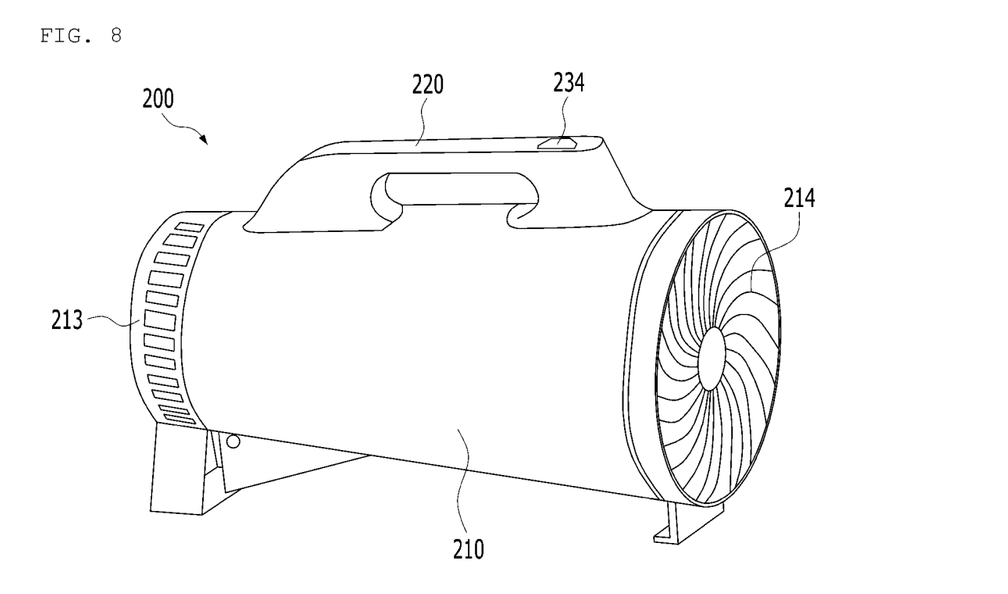
FIG. 8 is a perspective view illustrating a sterilization and disinfection device included in the portable sterilization and disinfection apparatus according to one embodiment the present invention.
Figure 9:
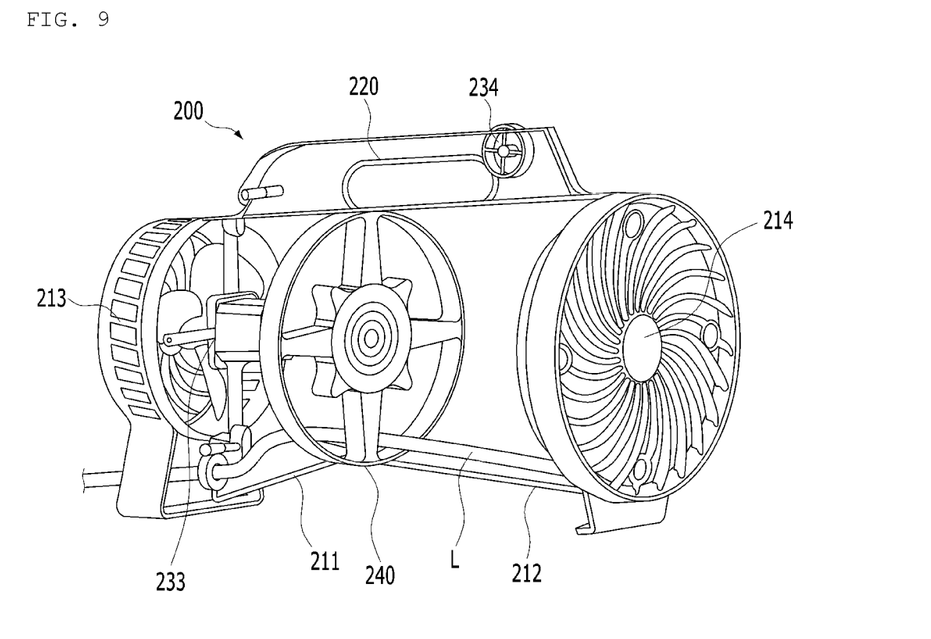
FIG. 9 is a partially-exploded perspective view of the sterilization and disinfection device included in the portable sterilization and disinfection apparatus according to one embodiment of the present invention, as seen from one side.
Figure 10:
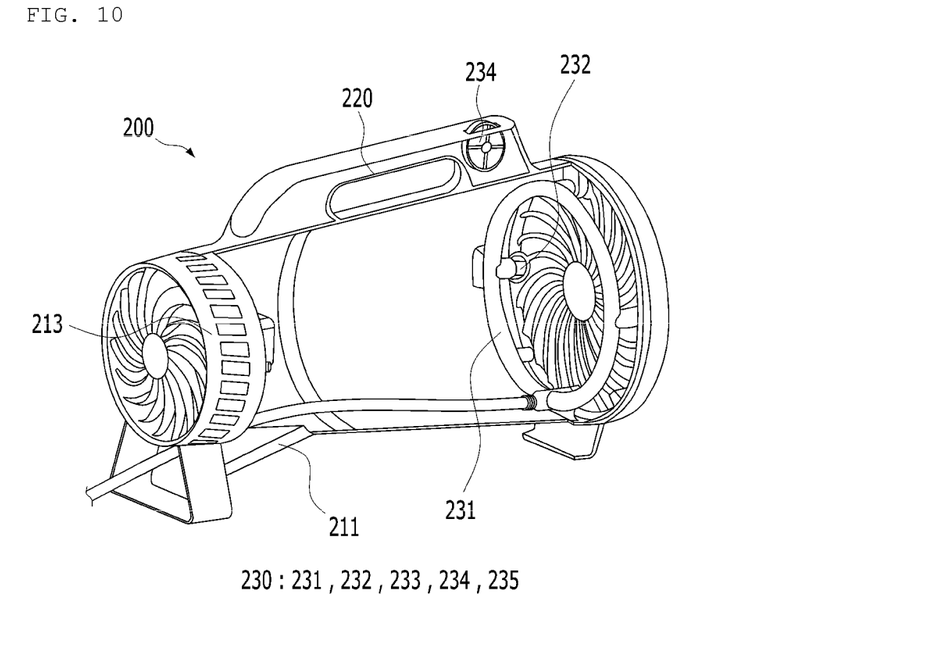
FIG. 10 is a partially-exploded perspective view of the sterilization and disinfection device included in the portable sterilization and disinfection apparatus according to one embodiment of the present invention, as seen from the other side.
Figure 11:
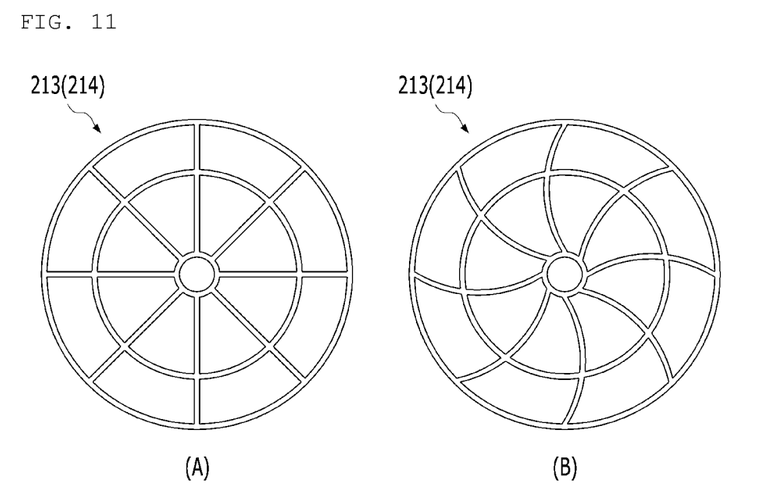
FIG. 11 shows views (A) and (B) illustrating the shapes of grill members of the sterilization and disinfection device included in the portable sterilization and disinfection apparatus according to one embodiment of the present invention.
Figure 12:
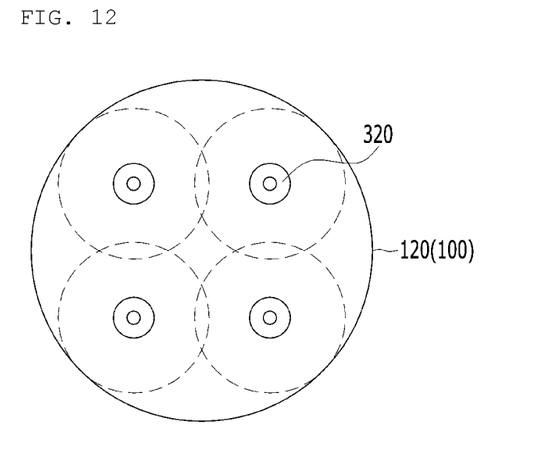
FIG. 12 is a diagram schematically illustrating nozzles and spray areas of the sterilization and disinfection device included in the portable sterilization and disinfection apparatus according to one embodiment of the present invention.

FIG. 8 is a perspective view illustrating the sterilization and disinfection device included in the portable sterilization and disinfection apparatus according to one embodiment the present invention, FIG. 9 is a partially-exploded perspective view of the sterilization and disinfection device included in the portable sterilization and disinfection apparatus according to one embodiment of the present invention, as seen from one side, FIG. 10 is a partially-exploded perspective view of the sterilization and disinfection device included in the portable sterilization and disinfection apparatus according to one embodiment of the present invention, as seen from the other side, FIGS. 11(A) and 11(B) are diagrams schematically illustrating nozzle and spray areas of the sterilization and disinfection device included in the portable sterilization and disinfection apparatus according to one embodiment of the present invention, and FIG. 12 is a view illustrating the shape of grill members of the sterilization and disinfection device included in the portable sterilization and disinfection apparatus according to one embodiment of the present invention.

The sterilization and disinfection device 200 is connected to the chemical liquid supply device 100 through the chemical liquid supply line L, and is configured to receive the chemical liquid for sterilization and disinfection from the chemical liquid supply device 100, to atomize the chemical liquid for sterilization and disinfection and to discharge the atomized chemical liquid for sterilization and disinfection.

Concretely, the sterilization and disinfection device 200 according to one embodiment of the present invention includes, as shown in FIGS. 8 to 12, a pipe-shaped casing 210 configured such that an airflow is formed therein, a handle frame 220 formed at one side of the casing 210 so as to be grasped by a worker, and an atomization blower unit 230 provided at one end of the casing 210 (the downstream end of the casing 210 in the airflow direction) and configured to atomize the chemical liquid for sterilization and disinfection supplied from the chemical liquid supply device 100 and to discharge the atomized chemical liquid for sterilization and disinfection.

The casing 210 includes a first expansion pipe part 211 having a conical shape, a second expansion pipe part 212 having a conical shape and formed to have a greater size than that of the first expansion pipe part 211, a first grill member 213 provided to cover the open end of the first expansion pipe part 211, and a second grill member 214 provided to cover the open end of the second expansion pipe part 212.

Here, the first expansion pipe part 211 and the second expansion pipe part 212 may be connected by a linear pipe-shaped part provided therebetween.

Further, although the first expansion pipe part 211 and the second expansion pipe part 212 may be formed integrally, the first expansion pipe part 211 and the second expansion pipe part 212 may be detachably combined with each other for the purpose of maintenance and repair. The same is applied in case that the linear pipe-shaped part is connected between the first expansion pipe part 211 and the second expansion pipe part 212.

The first grill member 213 and/or the second grill member 214 may have a shape in which a plurality of straight ribs is disposed radially, as shown in FIG. 11(A), or may have a shape in which a plurality of curved ribs is disposed radially in the form of a vortex, as shown in FIG. 11(B). The first grill member 213 and/or the second grill member 214 are not limited to these shapes, and may be formed in various shapes which may increase efficiency in straightness of sprayed particles.

The handle frame 220 is formed at one side of the casing 210, and more concretely, at the upper part of the casing 210, so as to be grasped by a worker.

Further, a control switch (i.e., a fan speed control switch 234 configured to adjust the speed of a blower fan 233), which may control operation of elements, requiring power control, of the atomization blower unit 230, which will be described in detail below, is provided on the handle frame 220. This will be described in detail below together with the description of the atomization blower unit 230.

Further, a power connection port, which is connected to the battery 152 of the chemical liquid supply device 100 by a power cable so as to receive power from the battery 152 and to supply the power to the blower fan 233 and a heater, may be formed in the handle frame 220, and a fastening part, to which a separate shoulder strap is connected so that a worker is capable of carrying the sterilization and disinfection device 200 on his/her shoulder, may be formed at the handle frame 220.

The atomization blower unit 230 is provided within the casing 210 and is configured to atomize the chemical liquid for sterilization and disinfection supplied from the chemical liquid supply device 100, and the atomization blower unit 230 roughly includes a distribution pipe 231, nozzles 232, the blower fan 233, the fan speed control switch 234 and a fan battery (not shown).

Concretely, the atomization blower unit 230 includes the distribution pipe 231 provided within one end of the casing 210, i.e., the first expansion pipe part 211 of the casing 210, and having a connector connected to the chemical liquid supply line L, a plurality of nozzles 232 provided at the distribution pipe 231 and configured to atomize the chemical liquid for sterilization and disinfection and to discharge the atomized chemical liquid for sterilization and disinfection, the blower fan 233 provided within the other end of the casing 210, i.e., the second expansion pipe part 212 of the casing 210, and operated by a control signal due to operation of the fan speed control switch 234, the fan speed control switch 234 provided on the handle frame 220 and operated to select the speed of the blower fan 233, and the fan battery (not shown) provided within the casing 210 and configured to provide power required to operate the blower fan 233.

Here, the fan speed control switch 234 may be configured to simultaneously provide a function of turning the blower fan 233 on/off, and the fan battery may be omitted, when the power connection port is connected to the battery 152 of the chemical liquid supply device 100 by the power cable so as to receive necessary power from the battery 152, as described above.

The distribution pipe 231 may be formed as a ring-shaped pipe, and may be fixed such that the outer circumferential surface thereof is spaced apart from the inner wall of the first expansion pipe part 211 of the casing 210 by a designated distance.

Because the distribution pipe 231 is spaced apart from the inner wall of the first expansion pipe part 211 of the casing 210 by the designated distance, the distribution pipe 231 is located at a position shown in FIG. 12, and thereby, collision of the chemical liquid for sterilization and disinfection atomized by the nozzles 232 with the first expansion pipe part 211 may be minimized and the chemical liquid for sterilization and disinfection may be blown by the blower fan 233 so as to be sprayed towards the entirety of a space to be sterilized and disinfected.

Further, the distribution pipe 231 may be formed of a thermally conductive material which may be heated by a heating member 240, which will be described below.

The nozzles 232 are not limited in terms of the interval between the nozzles 232 and the positions and number of the nozzles 232 on the distribution pipe 231.

The blower fan 233 may secure straightness in spraying, and may more firmly facilitate sterilization and disinfection of a target point in a target direction.

In addition, the sterilization and disinfection device 200 may further include temperature and humidity sensors provided on the casing 210, a control circuit module configured to receive temperature and humidity sensed by the temperature and humidity sensors, and the heating member 240 provided at one side of the inside of the casing 210 (preferably, a side of the inside of the casing 210 close to the distribution pipe 231) and configured to perform heating by a signal from the control circuit module based on the temperature and humidity detected by the temperature and humidity sensors.

The sterilization and disinfection apparatus having the above configuration according to the present invention may further include the temperature and humidity sensors and the heating member 240, thereby being capable of increasing the evaporation rate of sprayed droplets depending on ambient temperature and humidity, and thus being capable of performing more effective space sterilization and disinfection and appropriately coping with temperature and humidity depending on the season, such as use in winter.

Next, a sterilization and disinfection device according to another embodiment of the present invention will be described with reference to FIGS. 13 to 15.

Figure 13:
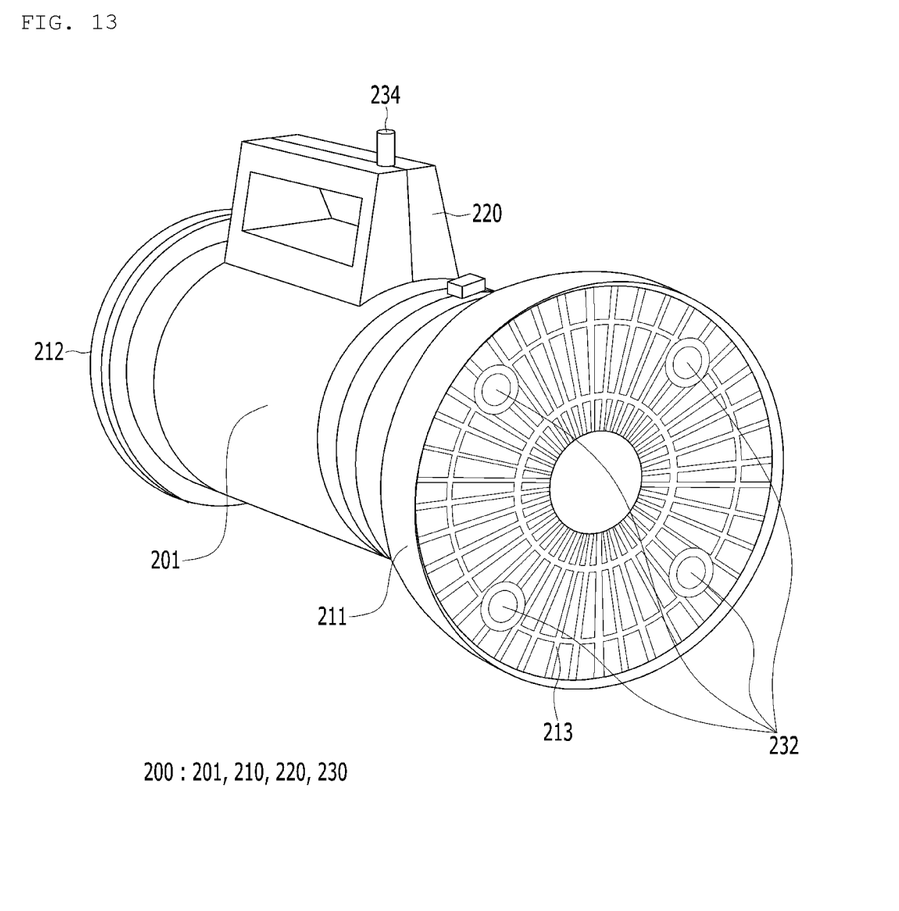
FIG. 13 is a perspective view of a sterilization and disinfection device included in a portable sterilization and disinfection apparatus according to another embodiment of the present invention, as seen from one side.
Figure 14:
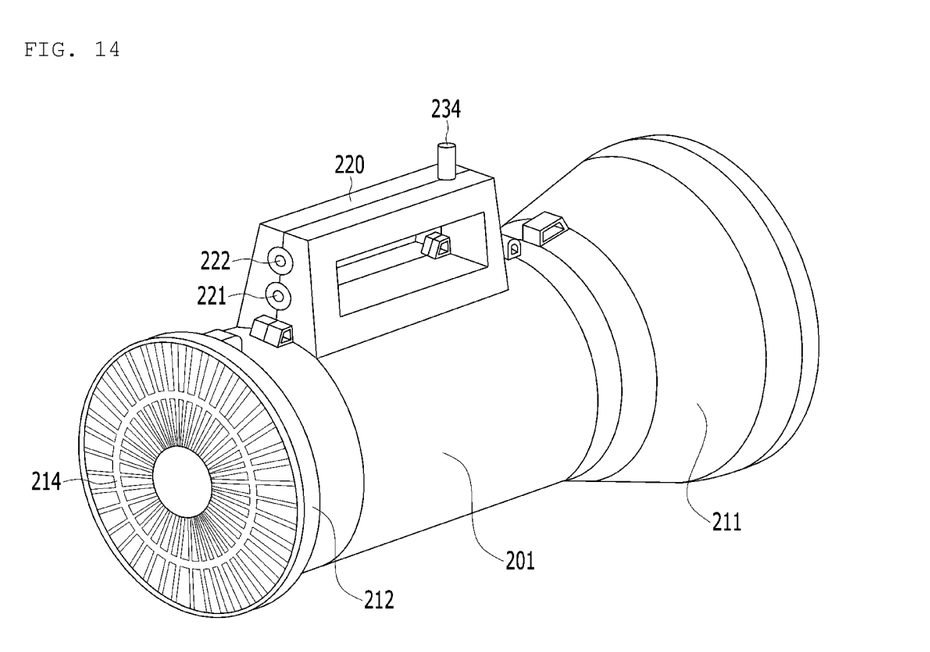
FIG. 14 is a perspective view of the sterilization and disinfection device included in the portable sterilization and disinfection apparatus according to another embodiment of the present invention, as seen from the other side.
Figure 15:
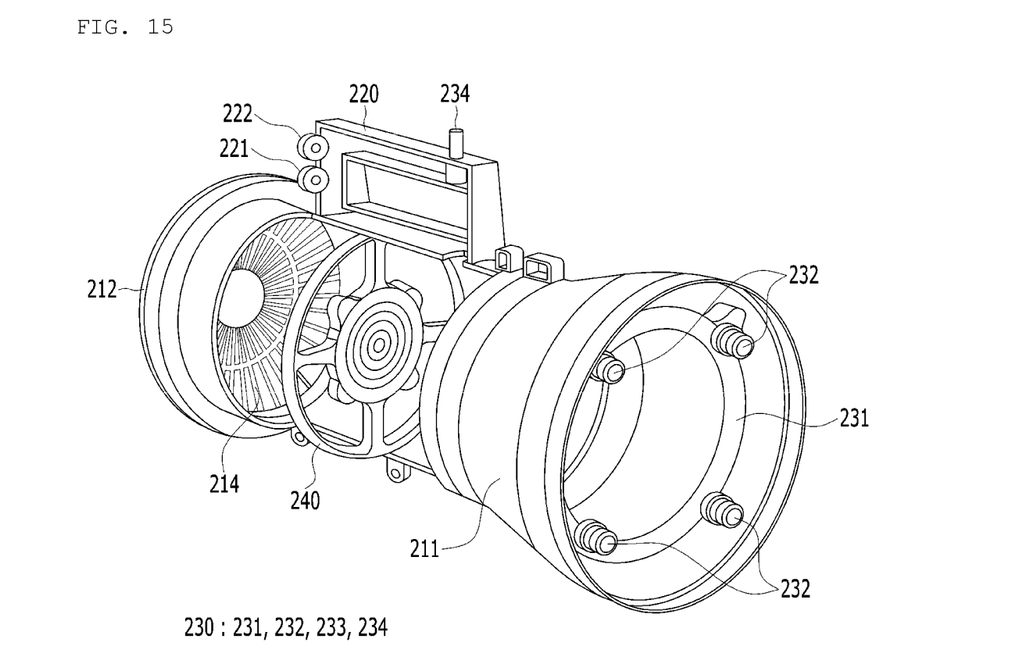
FIG. 15 is a partially-exploded perspective view of the sterilization and disinfection device included in the portable sterilization and disinfection apparatus according to another embodiment of the present invention.

FIG. 13 is a perspective view of a sterilization and disinfection device included in a portable sterilization and disinfection apparatus according to another embodiment of the present invention, as seen from one side, FIG. 14 is a perspective view of the sterilization and disinfection device included in the portable sterilization and disinfection apparatus according to another embodiment of the present invention, as seen from the other side, and FIG. 15 is a partially-exploded perspective view of the sterilization and disinfection device included in the portable sterilization and disinfection apparatus according to another embodiment of the present invention.

Some parts of the sterilization and disinfection device 200 according to another embodiment, which are substantially the same as those of the sterilization and disinfection device 200 according to the former embodiment, will be denoted by the same reference numerals even though they are depicted in different drawings.

The sterilization and disinfection device 200 according to another embodiment may roughly include a casing 210, a handle frame 220 and an atomization blower unit 230, and may further include elements configured to detect temperature and humidity so as to control atomization.

Concretely, the sterilization and disinfection device 200 according to another embodiment includes, as shown in FIGS. 13 to 15, the pipe-shaped casing 210 configured such that an airflow is formed therein, the handle frame 220 formed at one side of the casing 210 so as to be grasped by a worker, and the atomization blower unit 230 provided at one end of the casing 210 (the downstream end of the casing 210 in the airflow direction) and configured to atomize the chemical liquid for sterilization and disinfection supplied from the chemical liquid supply device 100 and to discharge the atomized chemical liquid for sterilization and disinfection.

The casing 210 includes a linear pipe-shaped part 201 configured to form the central portion of the casing 210, a first expansion pipe part 211 having a conical shape and provided at one end of the linear pipe-shaped part 201 (the downstream end of the linear pipe-shaped part 201 in the airflow direction), a second expansion pipe part 212 having a conical shape and provided at the other end of the linear pipe-shaped part 201 (the upstream end of the linear pipe-shaped part 201 in the airflow direction), a first grill member 213 provided to cover the open end of the first expansion pipe part 211, and a second grill member 214 provided to cover the open end of the second expansion pipe part 212.

Although the linear pipe-shaped part 201, the first expansion pipe part 211 and the second expansion pipe part 212 may be formed integrally, the linear pipe-shaped part 201, the first expansion pipe part 211 and the second expansion pipe part 212 may be detachably combined with each other for the purpose of maintenance and repair.

The first grill member 213 and/or the second grill member 214 may have a shape in which a plurality of straight ribs is disposed radially, or may have a shape in which a plurality of curved ribs is disposed radially in the form of a vortex, in the same manner as the former embodiment (with reference to FIGS. 11(A) and 11(B)). The first grill member 213 and/or the second grill member 214 are not limited to these shapes, and may be formed in various shapes which may increase efficiency in straightness of sprayed particles.

A chemical liquid connection port 221 configured to receive the chemical liquid for sterilization and disinfection pumped by the chemical liquid supply device 100 is formed in the handle frame 220 of the casing 210.

The handle frame 220 is formed at one side of the casing 210, and more concretely, at the linear pipe-shaped part of the casing 210, so as to be grasped by a worker.

Further, an operating controller, which may control operation of elements, requiring power control, of the atomization blower unit 230, which will be described in detail below, is provided on the handle frame 220. This will be described in detail below together with the description of the atomization blower unit 230.

Further, the chemical liquid connection port 221, which is connected to a chemical liquid supply line L, and a power connection port 222, which is connected to the battery 152 of the chemical liquid supply device 100 by a power cable so as to receive power from the battery 152 and to supply the power to a blower fan and a heater, are formed in the handle frame 220.

Here, a fastening part, to which a separate shoulder strap is connected so that a worker is capable of carrying the sterilization and disinfection device 200 on his/her shoulder, may be formed at the handle frame 220.

The atomization blower unit 230 is provided at one end of the casing 210 (the downstream end of the casing 210 in the airflow direction) and is configured to atomize the chemical liquid for sterilization and disinfection supplied from the chemical liquid supply device 100 and to discharge the atomized chemical liquid for sterilization and disinfection.

The atomization blower unit 230 roughly includes a distribution pipe 231, a supply pipe (not shown), nozzles 232, a blower fan (not shown), a control circuit module (not shown), and a fan speed control switch 234.

Concretely, the atomization blower unit 230 includes the distribution pipe 231 provided within one end of the casing 210, i.e., the first expansion pipe part 211 of the casing 210, and configured to receive the chemical liquid for sterilization and disinfection, the supply pipe (not shown) provided with one end connected to the chemical liquid connection port 221 formed in the handle frame 220 and the other end connected to the distribution pipe 231 so as to supply the chemical liquid for sterilization and disinfection introduced from the chemical liquid supply device 100 to the distribution pipe 231, a plurality of nozzles 232 provided at the distribution pipe 231 and configured to atomize the chemical liquid for sterilization and disinfection and to discharge the atomized chemical liquid for sterilization and disinfection, the blower fan (not shown, with reference to FIG. 9) provided within the other end of the casing 210, i.e., the second expansion pipe part 212 of the casing 210, and operated by a control signal from the control circuit module due to operation of the fan speed control switch 234, the control circuit module (not shown) provided on the handle frame 220 so as to control operation of the blower fan, the fan speed control switch 234 provided on the handle frame 220 and operated to select the speed of the blower fan and to transmit an operation signal to the control circuit module, and a fan battery (not shown) configured to provide power required to operate the blower fan.

The distribution pipe 231 may be formed as a ring-shaped pipe, and may be fixed such that the outer circumferential surface thereof is spaced apart from the inner wall of the first expansion pipe part 211 of the casing 210 by a designated distance.

Because the distribution pipe 231 is spaced apart from the inner wall of the first expansion pipe part 211 of the casing 210 by the designated distance in the same manner as in the former embodiment, collision of the chemical liquid for sterilization and disinfection sprayed by the nozzles 232 with the first expansion pipe part 211 may be minimized, and the chemical liquid for sterilization and disinfection may be sprayed towards the entirety of a space to be sterilized and disinfected.

Further, the distribution pipe 231 may be formed of a thermally conductive material which may be heated by a heating member 240, which will be described below.

The nozzles 232 are not limited in terms of the interval between the nozzles 232 and the positions and number of the nozzles 232 on the distribution pipe 231.

The blower fan 233 may secure straightness in spraying, and may more firmly facilitate sterilization and disinfection of a target point in a target direction.

In the same manner as the former embodiment, the sterilization and disinfection device 200 according to this embodiment may further include temperature and humidity sensors (not shown) provided at one side of the casing 210 and configured to transmit sensed temperature and humidity to the control circuit module, and the heating member 240 provided on the distribution pipe 231 and configured to perform heating by a signal from the control circuit module based on the temperature and humidity sensed by the temperature and humidity sensors.

The sterilization and disinfection apparatus according to this embodiment may further include the temperature and humidity sensors and the heating member 240, thereby being capable of increasing the evaporation rate of sprayed particles depending on ambient temperature and humidity, and thus being capable of performing more effective space sterilization and disinfection and appropriately coping with temperature and humidity depending on the season, such as use in winter.

As is apparent from the above description, a portable sterilization and disinfection apparatus for sterilizing and disinfecting a space according to the present invention may provide the following effects.

First, the portable sterilization and disinfection apparatus according to the present invention sprays particles of a diameter of 5-50 μm and may thus increase the floating time of the particles and increase sterilization efficiency due to high probability of contact between the particles and bacteria and virus in the air, and enable sterilization and disinfection of a wide space as well as simple insecticide action and disinfection.

Second, the portable sterilization and disinfection apparatus according to the present invention may increase the sprayed capacity of a chemical liquid for sterilization and disinfection using superhigh pressure, and may increase sterilization efficiency due to the high rate of sprayed particles which are effective in sterilization.

Third, the portable sterilization and disinfection apparatus according to the present invention may enable ultrafine spray so as to prevent droplets caused by spray from falling around the apparatus, and prevent waste of the chemical liquid for sterilization and disinfection so as to effectively use the chemical liquid for sterilization and disinfection.

Fourth, the portable sterilization and disinfection apparatus according to the present invention enables freely oriented spray in a desired direction, and may thus intensively sterilize a target local point or area to be sterilized and disinfected as well as a relatively wide space.

Fifth, the portable sterilization and disinfection apparatus according to the present invention may expand a spraying distance, and may thus sterilize and disinfect a space at a long distance to which a worker cannot come close.

Sixth, the portable sterilization and disinfection apparatus according to the present invention has a light weight, and may thus be freely moved to any area or place so as to easily sterilize and disinfect the area or the place.

Seventh, the portable sterilization and disinfection apparatus according to the present invention may automatically control sterilization and disinfection depending on ambient temperature and humidity, thereby being capable of more effectively sterilizing and disinfecting a space.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A portable sterilization and disinfection apparatus for sterilizing and disinfecting a space, the portable sterilization and disinfection apparatus comprising:
   a chemical liquid supply device configured to store a chemical liquid for sterilization and disinfection and to supply the stored chemical liquid for sterilization and disinfection; and
   a sterilization and disinfection device connected to the chemical liquid supply device through a chemical liquid supply line and configured to receive the chemical liquid for sterilization and disinfection from the chemical liquid supply device, to atomize the chemical liquid for sterilization and disinfection, and to discharge the chemical liquid for sterilization and disinfection,
   wherein the sterilization and disinfection device comprises:
      a casing provided with a first grill member and a second grill member provided at both ends of the casing so that air is flowable outwards therethrough, the casing comprising a linear pipe-shaped part configured to form a central portion of the casing, a first expansion pipe part having a conical shape and provided at one end of the linear pipe-shaped part, a second expansion pipe part having a conical shape and provided at a remaining end of the linear pipe-shaped part;

a handle frame formed at one side of the casing and configured to be grasped by a worker;

temperature and humidity sensors provided on the casing;

a heating member formed as a circular ring with one end of the circular ring meeting the other end to form a closed loop; and an atomization blower unit provided at one end of the casing and configured to atomize the chemical liquid for sterilization and disinfection supplied from the chemical liquid supply device and to discharge the atomized chemical liquid for sterilization and disinfection, wherein the atomization blower unit comprises:

a distribution pipe distribution pipe formed as a ring-shaped pipe, wherein the distribution pipe is fixed such that an outer circumferential surface of the distribution pipe is spaced apart from an inner wall of the casing, and located within one end of the casing to receive the chemical liquid for sterilization and disinfection, wherein the distribution pipe is made of a thermally conductive material which is heated by the heating member as the heating member is located adjacent to the distribution pipe;

a chemical liquid connection port provided in the handle frame and configured such that the chemical liquid supply line is connected to the chemical liquid connection port;

a supply pipe provided between the distribution pipe and the chemical liquid connection port so as to connect the distribution pipe and the chemical liquid connection port;

a plurality of nozzles provided at the distribution pipe and configured to atomize the chemical liquid for sterilization and disinfection and to discharge the atomized chemical liquid for sterilization and disinfection;

a blower fan provided within the casing and operated to blow air;

a control circuit module provided on the handle frame and configured to control operation of the blower fan, wherein the temperature and humidity sensors are configured to transmit detected signals to the control circuit module, wherein the heating member is configured to perform heating by a control signal from the control circuit module, wherein a power connection port configured such that a power cable is connected thereto so as to supply power to the control circuit module is formed in the handle frame;

a fan speed control switch configured to control turning-on/off of the blower fan and a speed of the blower fan; and a fan battery provided within the casing and configured to provide power required to operate the blower fan.

2. The portable sterilization and disinfection apparatus according to claim 1, wherein the chemical liquid supply device comprises:

a box-shaped body;

a body cover combined with the body so as to open and close the body;

a chemical liquid storage tank provided within the body;

a pump provided within the body and configured to pump the chemical liquid for sterilization and disinfection from the chemical liquid storage tank so as to supply the chemical liquid for sterilization and disinfection to the sterilization and disinfection device;

a battery unit provided within the body and configured to provide power required to operate the pump; and a control switch provided on the body and configured to control operation of the pump.

3. The portable sterilization and disinfection apparatus according to claim 2, wherein:

the body comprises a handle member provided at one side of an upper end of the body or an upper end of a rear surface of the body and configured to extend and contract in a telescopic manner so as to be received in the body, and rolling wheels provided at a lower end of the body;

the body cover is configured to open and close the body in a sliding manner.

4. The portable sterilization and disinfection apparatus according to claim 2, wherein the battery unit comprises a battery support provided at one side of a lower portion of the body, and a battery detachably fixed to the battery support, wherein the battery support is provided on an inner wall of one side of the lower portion of the body so as to be foldable at an angle of 90°.

* * * * *